United States Patent
Mühlbauer

(10) Patent No.: US 6,638,540 B2
(45) Date of Patent: *Oct. 28, 2003

(54) PLANT EXTRACTS FOR THE TREATMENT OF INCREASED BONE RESORPTION

(75) Inventor: Roman Conrad Mühlbauer, Rapperswil (SE)

(73) Assignee: Universitat Bern, Bern (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,245

(22) PCT Filed: May 4, 1998

(86) PCT No.: PCT/EP98/02627

§ 371 (c)(1),
(2), (4) Date: Nov. 4, 1999

(87) PCT Pub. No.: WO98/50054

PCT Pub. Date: Nov. 12, 1998

(65) Prior Publication Data

US 2003/0185905 A1 Oct. 2, 2003

(30) Foreign Application Priority Data

May 6, 1997 (GB) .............................................. 9709082

(51) Int. Cl.⁷ .............................................. A61K 35/78
(52) U.S. Cl. ........................ 424/725; 424/775; 424/754
(58) Field of Search ............................ 424/195.1, 94.1, 424/556, 648, 655, 563, 725, 775, 774

(56) References Cited

U.S. PATENT DOCUMENTS

| | | | | |
|---|---|---|---|---|
| 4,088,790 A | * | 5/1978 | Bevan et al. | 426/96 |
| 4,772,591 A | * | 9/1988 | Meisner | 514/62 |
| 4,786,510 A | * | 11/1988 | Nakel et al. | 426/72 |
| 4,976,960 A | | 12/1990 | Grossman et al. | 424/195 |
| 5,244,662 A | | 9/1993 | Han et al. | 424/195 |
| 5,424,331 A | | 6/1995 | Shlyankevich | 514/456 |
| 5,494,668 A | | 2/1996 | Patwardhan | 424/195 |
| 5,506,211 A | | 4/1996 | Barnes et al. | 514/27 |
| 5,569,459 A | | 10/1996 | Shlyankevich | 424/195 |
| 5,895,652 A | * | 4/1999 | Giampapa | 424/195.1 |
| 5,961,981 A | | 10/1999 | Gutierrez | 424/195 |
| 6,149,939 A | * | 11/2000 | Strumor et al. | 424/464 |

FOREIGN PATENT DOCUMENTS

| | | | |
|---|---|---|---|
| EP | 0 745 332 | | 12/1996 |
| FR | 2728168 A1 | * | 6/1996 |
| JP | 3019630 | | 1/1991 |
| JP | 04211609 | | 8/1992 |
| JP | 5130583 | | 5/1993 |
| JP | 06183985 | | 5/1994 |
| JP | 6192116 | | 7/1994 |
| JP | 05017229 | * | 8/1994 ............. 424/195.1 |
| JP | 6225723 | | 8/1994 |
| JP | 06340542 | | 12/1994 |
| JP | 7017845 | | 1/1995 |
| JP | 7101859 | | 4/1995 |
| JP | 07101868 | | 4/1995 |
| JP | 8099890 | | 4/1996 |
| JP | 08231533 | | 9/1996 |
| JP | 8259457 | | 10/1996 |
| JP | 09030977 | | 2/1997 |
| SK | 1088108 | | 6/1994 |
| SU | 730338 | | 5/1980 |
| SU | 1658977 | | 6/1991 |
| WO | 92/07575 | | 5/1992 |
| WO | 94/05306 | | 3/1994 |
| WO | 94/05307 | | 3/1994 |
| WO | 94/07513 | | 4/1994 |
| WO | WO 96/31130 | | 10/1996 |
| ZA | 9500908 | | 12/1995 |

OTHER PUBLICATIONS

Thomas et al. Quantification of ALK(EN)YL–LCysteine Sulfoxides and Related Amino Acids in Alliums by High–Performance Liquid Chromatography; vol. 42, No. 8 (Abstract), 1994.*

Robbins, J. Cream of Broccoli Soup; May All Be Fed, Morrow, W. ed., 1992, from The Recipe Source: www.recipesource.com/soups/soups/09/rec0920.html, accessed May 19, 2002.*

Lust, J.; The Herb Book; Bantam Books, pp. 494–495 and 501, 1974.*

M.L. Brandi, "Natural and Synthetic Isoflavones in the Prevention and Treatment of Chronic Diseases", (1997), Calcifiedssue International, 61 Suppl 1 S5–8, Ref: 42.

A. Brzezinski, et al., "Short–term Effects of Phytoestrogen–rich Diet on Postmenopausal Women", (1997), Menopause: The Journal of The North American Menopause Society, vol. 4, No. 2, pp. 89–94.

A. Cassidy, "Physiological Effects of Phyto–Oestrogens in Relation to Cancer and Other Human Health Risks", (1996), Proceedings of the Nutrition Society, 55, 399–417.

Y.P. Chen, "Pharmacological Study on Chinese Medicinal Herbs Used in Orthopedics and Iraumatology", (1986), Chung Yao Tung Pao Bulletin of Chinese Materia Medica, 11(7) 3–6. (Medline only).

B. Donn, et al., "Inhibition of Matrix Metalloproteinases: Therapeutic Potential", (1994) Annals of the New York Academy of Sciences, vol. 732, p. 379.

(List continued on next page.)

Primary Examiner—Jon P. Weber
Assistant Examiner—Patricia Patten
(74) Attorney, Agent, or Firm—John W. Kung

(57) ABSTRACT

The present invention is concerned with nutritional or pharmaceutical compositions containing a plant extract or concentrate selected from the group consisting of allium (leek), aethusa (dog parsley), petroselium (parsley) and brassica (cabbage) extracts and concentrates. The compositions of the invention are useful for the treatment or prophylaxis of diseases or conditions which are characterized by increased bone resorption, such as Paget's disease, tumor-induced bone disease or particularly osteoporosis.

24 Claims, No Drawings

OTHER PUBLICATIONS

C.R. Draper, et al., "Phytoestrogens Reduce Bone Loss and Bone Resorption in Oophorectomized Rats", (1997) American Society for Nutritional Sciences, pp. 1795–1799.

T. Hatano, et al., "Camelliatannin D, A New Inhibitor of Bone Resorption, from *Camellia japonica*", (1995) Chemical and Pharmaceutical Bulletin, (11) 2033–5.

D.C. Knight, et al., "Phytoestrogens—A Short Review", (1995) Maturitas, (3) 167–75, Ref: 89.

D.C. Knight, et al., "A Review of the Clinical Effects of Phytoestrogens", (1996), Obstetrics and Gynecology, 87 (5 Pt 2) 897–904, Ref: 90.

D. Kraft, et al., "The Effect of Solanum Malacoxylon on Rachitic Bone Lesions in the Rat", (1975), Naunyn–Schmiedeberg's Archives of Pharmacology, 290 (1) 29–33.

C.Y. Li, "Effects of Fructus Cnidii Coumarins Compared with Nolestriol", (1997), Acta Pharmacologica Sinica, Vol/ISS: 18/3, pp.: 286–288. (Chinese with Some English.).

W. Lloyd, et al., "Stimulation of Bone Resorption in Organ Culture by Salt–free Extracts of Solanum Glaucophyllum", (1975), Endocrine Research Communications, 2 (2) 159–66.

M. Messina, "Modern Applications for an Ancient Bean: Soybeans and the Prevention and Treatment of Chronic Disease", (1995), J. Nutrition, Vol/ISS: 125/3Sup, pp.: 567S–569.

H. Miura, "Effect of Crude Fractions of Psorales Corylifolia Seed Extract on Bone Calcification", (1996), Planta Medica, 62 (2) 150–3.

J. Porte, et al., "Clinical and Ultrastructural Study of the Action of Unsaponifible Cornseed Oil in a Case of Periodontolysis in Man", (1978), Actualites Odonto–Stomatologiques, (121) 125–39. (Medicine only).

A.F. Raonimala, et al., "Action of Soluble Carbohydrates from Avocado (Persea Gratissima Gaertner) Fruit on Utilization of Calcium in the Rat", (1980), Annales De La Nutrition Et De L Alimentation, 34 (4) 735–44. (Medline abstract).

M.N. Santos, et al., "Solanum Malacoxylon Toxicity: Inhibition of Bone Resorption", (1976), Cornell Veterinarian, 66 (4) 566–89.

M.I. Skliar, et al., "Osteolytic Activity and Reversal of Nephrectomy–Induced Hypocalcemia by a Fraction Other Than $1,25(OH)_2$–Vitamin $D_3$ from Solanum Malacoxylon Incubated with Ruminal Fluid", (1994), Hormone and Metabolic Research, 26 (9) 424–7.

M. Taylor, MD, "Alternatives to Conventional Hormone Replacement Therapy", (1997), Comp Ther., 23 (8):54–532.

H. Tobe, "Bone Resorption Inhibitors from Hop Extract", (1997) Bioscience Biotechnology Biochemistry, Vol/ISS: 61/1, pp.: 158–159.

A. Wachman, et al., "Diet and Osteoporosis", (1968), Lancet, 1 (549) 958–9.

C.M. Weaver, "Calcium Bioavailability and Its Relation to Osteoporosis", (1992), Proceedings of the Society for Experimental Biology and Medicine, 200 (2) 157–60.

H. Adlercreutz, et al., "Phyto–oestrogens and Western Diseases", (1997), The Finnish Medical Society DUODECIM, Ann Med 29, 95–120.

R. Ansbacher, MD, MS, "Nonestrogenic Therapy for the Menopause", (1995), Comprehensive Therapy, 21(5);242–244.

J. Barrett, "Phytoestrogens. Friend or foes?" (news), (1996) Environmental Health Perspectives, vol/ISS: 104/5, pp.: 478–482.

* cited by examiner

PLANT EXTRACTS FOR THE TREATMENT OF INCREASED BONE RESORPTION

This application is a United States national stage filing of International Application No. PCT/EP98/02627, filed on May 4, 1998, which claims priority under 35 USC 119 from GB patent application 9709082.3, filed on May 6, 1997.

The present invention relates to nutritional or pharmaceutical compositions comprising extracts or concentrates of certain plants and their use as inhibitors of bone resorption.

The most common metabolic bone disorder is osteoporosis. Osteoporosis can be generally defined as the reduction in the quantity of bone, either from the reduction in bone formation or the acceleration of bone resorption, in either event the result is a decrease in the amount of skeletal tissue. Osteoclasts (bone resorbing cells) are responsible for the excavation of a portion of bone during the resorption process. After resorption, osteoblasts (bone forming cells) appear, which then refill the resorbed portion with new bone.

In young healthy adults, the rate at which the osteoclasts and osteoblasts are formed and operate maintains a balance between bone resorption and bone formation. However, as normal consequence of aging, an imbalance in this remodeling process develops, resulting in loss of bone. As imbalance continues over time, the reduction in bone mass and thus bone strength leads to fractures.

Many compositions and methods are described in the medical literature for the treatment of osteoporosis. For example, estrogens, calcitonin and bisphosphonates are known to be effective inhibitors of bone resorption.

It has now surprisingly been found that products derived from certain plants or vegetables which belong for example to the botanical families of liliaceae, umbelliferae and cruciferae have a potent inhibitory effect on bone resorption.

Accordingly, the present invention relates to the use of a vegetable extract or concentrate, excluding extracts or concentrates derived from leguminosae and hop, having an inhibitory effect on bone resorption in the preparation of a medicament or nutritional formulation for the treatment or prophylaxis of a disease or condition which is characterized by increased bone resorption, such as Paget's disease, tumor-induced bone disease or particularly osteoporosis.

By the term leguminosae is meant the botanical family leguminosae (pea family) which includes for example soybean, beans, chick pea or lentil. By hop is meant the botanical species Humulus lupulus.

Osteoporosis as used herein includes osteoporosis induced by hormone deficiency (e.g. postmenopausal) and old age, as well as secondary osteoporosis such as osteoporosis secondary to steroid treatment or secondary to malnutrition caused by anorexia nervosa.

The invention further provides a method for the treatment or prophylaxis of a disease or condition which is characterized by increased bone resorption, such as Paget's disease, tumor-induced bone disease or particularly osteoporosis, comprising the administration of a medicament or nutritional formulation to a human or other mammal, said medicament or nutritional formulation comprising a vegetable extract or concentrate, excluding extracts or concentrates derived from leguminosae and hop, in an amount which is effective for inhibiting bone resorption.

The present invention also foresees the use of an extract or concentrate from a plant selected from the group consisting of allium, petroselinum, brassica and eruca extracts and concentrates in the preparation of a medicament or nutritional formulation for the treatment or prophylaxis of a disease or condition which is characterized by increased bone resorption, such as Paget's disease, tumor-induced bone disease or particularly osteoporosis.

Also provided is a method for the treatment or prophylaxis of a disease or condition which is characterized by increased bone resorption, such as Paget's disease, tumor-induced bone disease or particularly osteoporosis, comprising the administration of a medicament or nutritional formulation to a human or other mammal, said medicament or nutritional formulation comprising an extract or concentrate from a plant selected from the group consisting of allium, petroselinum, brassica and eruca extracts and concentrates, in an amount which is effective for inhibiting bone resorption.

Preferably the extracts and concentrates from allium, petroselinum, brassica and/or eruca are vegetable extracts or concentrates.

As used herein, the term vegetable refers to a herbaceous plant which has an edible portion which is consumed by humans in either raw or cooked form. The edible portion may be a root, such as rutabaga, beet, carrot, and sweet potato; a tuber or storage stem, such as potato and taro; the stem, as in asparagus and kohlrabi; a bud, such as brussels sprouts; a bulb, such as onion and garlic; a petiole or leafstalk, such as celery and rhubarb; a leaf, such as cabbage, lettuce, parsley and spinach; an immature flower, such as cauliflower, broccoli and artichoke; a seed; the immature fruit, such as eggplant, cucumber, and sweet corn (maize); or the mature fruit, such as tomato and pepper.

As used herein, the term allium refers to the genus allium (latin for garlic, a member of the onion family) and includes for example any member of the botanical species *Allium cepa* (onion), *Allium ascalonicum* (shallot), *Allium ampeloprasum* (leek/great-headed-garlic), *Allium porrum* (leek), *Allium schoenoprasum* (chive), *Allium ursinum* (bear's garlic), *Allium sativum* (garlic) or *Allium fistulosum* (bunching onion). Preferred species are *Allium ascalonicum* (shallot), *Allium porrum* (leek), *Allium cepa* (onion) and *Allium ursinum* (bear's garlic, also known as bear paw garlic), particularly the latter two, whereby *Allium cepa* is particularly preferred. Examples of members of the species *Allium cepa* are common onions (with red or white or yellow skins) or shallots, whereby red or white common onions are preferred.

The onion extracts and concentrates are prepared e.g. from the whole eatable part of the vegetable. Suitable chive extracts and concentrates are obtained e.g. from chive herbs. Suitable bear's garlic extracts and concentrates are obtained e.g. from bear's garlic bulbs, fresh herbs or from the whole blooming plant, preferably they are obtained form fresh herbs.

The term petroselinum as used herein refers to the genus petroselinum (common name parsley) and includes for example any member of the botanical species *Petroselinum crispum*. Examples are *Petroselinum crispum crispum*, that is common parsley with curly leaves, *Petroselinum crispum radiosum* or *Petroselinum crispum* var. neapolitanum also known as Italian Parsley with flat leaves.

Suitable petroselinum extracts or concentrates may be produced e.g. from roots, fruits or seeds, or particularly from herbs.

As used herein the term brassica refers to the genus brassica (latin for cabbage) and includes for example any member of the botanical species *Brassica oleracea, Brassica napus, Brassica rapa, Brassica alboglabra, Brassica juncea, Brassica perviridis, Brassica alba* and *Brassica nigra*.

*Brassica oleracea* is a preferred species, particularly preferred members of this species are *Brassica oleracea* var.

italica, i.e. broccoli, or *Brassica oleracea* var. gemmifera, i.e. Brussels sprouts. Broccoli extracts and concentrates are particularly preferred as brassica extract or concentrate. Suitable extracts and concentrates of brassica oleraceae species are produced advantageously from the whole eatable part of the vegetable or from the freshly germinated sprouts or shoots.

As used herein the term eruca refers to the genus eruca and includes in particular any member of the botanical species *Eruca sativa* (wild form) or *Eruca vesicaria* subsp. sativa (cultivated form) for which the common name is arrugula or roquette.

The plant/vegetable extracts and concentrates of the invention are preferably obtained from an edible portion of the plant or vegetable. By edible portion is meant the portion which is consumed by humans in either raw or cooked form.

A preferred group of inventive plant/vegetable extracts and concentrates comprises concentrates or extracts from any member of the botanical species *Allium cepa, Allium ascalonicum, Allium ursinum, Petroselinum crispum, Brassica oleracea* or *Eruca sativa*. A more preferred group of inventive plantvegetable extracts and concentrates comprises extracts and concentrates from any member of the botanical species *Allium cepa, Petroselinum crispum* (in particular *Petroselinum crispum crispum* and *Petroselinum crispum* var. neapolitanum) and *Brassica oleracea* (in particular *Brassica oleracea* var. italica), particularly extracts and concentrates of onions (*Allium cepa*), Italian Parsley (*Petroselinum crispum* var. neapolitanium) or broccoli (*Brassica oleracea* var. italica). The use of onion extracts (in particular white onion extracts) is particularly preferred.

The extracts and concentrates of the above-mentioned plants or vegetables may be in liquid form or in solid form such as in granulate or powder form.

Suitable plant or vegetable concentrates are obtainable e.g. by drying or freeze-drying the fresh-cut plants or vegetables or the respective roots, fruits or seeds thereof and then optionally grinding or granulating the dried material; or by squeezing the fresh-cut plants or vegetables or the respective roots, fruits or seeds thereof and gathering the liquid fraction and optionally drying it. The use of a concentrate of the above-mentioned plants or vegetables in solid form and particularly in powder form is preferred.

Suitable methods of obtaining extracts of the above-mentioned plants or vegetables are known in the art. The plant or vegetable extracts are obtainable e.g. by extracting the fresh-cut or dried plants or vegetables or the respective roots, fruits or seeds thereof for example with water or with one or more food grade solvents or with a mixture of water and one or more food grade solvents. Suitable food grade solvents include propane, butane, butyl acetate, ethyl acetate, ethanol, carbon dioxide, acetone, nitrous oxide, methanol and propan-2-ol, whereby ethanol and carbon dioxide are preferred; ethanol is a particularly preferred food grade solvent. After the extraction step the liquid phase is optionally concentrated or dried by evaporation or freeze drying. The fresh-cut or dried plant or vegetable material may be introduced in cold or preferably hot water and/or solvent, preferably water or a mixture of water with one or more solvents, for a specified period of time, which may vary within wide ranges depending on the kind of plant or vegetable material or solvent used but commonly amounts for example to 1 to 30 minutes, preferably 2 to 15 minutes and most preferred 5 to 10 minutes for a water extraction and for example 30 to 90 minutes, preferably 60 minutes for an ethanol/water extraction. For a water extraction the temperature preferably lies in the range of 85 to 95° C. and for an alcohol/water extraction the temperature preferably lies in the range of 55 to 65° C. For a carbon dioxide extraction, the extraction preferably takes place at 0 to 40° C. and at super-critical pressure (e.g. 80–200 bar). After the extraction the liquid phase is separated and advantageously concentrated or evaporated to dryness according to known methods. To obtain a concentrated extract two or more extraction steps as described above may be combined. Moreover, the plant or vegetable extracts may be obtained by introducing the fresh-cut or dried plant or vegetable in water and subjecting the mixture to a steam distillation. The distillate is collected and is then advantageously concentrated or evaporated to dryness.

The extract may be used in liquid form, particularly in aqueous form, or in solid form, particularly in granulate or powder form. If the extract is in liquid form, it has a solid contents of for example from 1 to 25% by weight, preferably from 2 to 20% by weight and most preferred from 2 to 15% by weight.

The amount of inventive plant/vegetable extract or concentrate to be supplied may vary within wide ranges, depending on i.a. the desired treatment, subject to be treated and his needs. Thus, where the subject to be treated is an adult person (typically of ca. 60 to 75 kg body weight), a satisfactory inhibitory effect on bone resorption is, in general obtained with compositions formulated to allow a daily administration of 0.1 to 20 grams, preferably 0.2 to 15 grams and most preferred 0.4 to 10 grams of allium, petroselinum, brassica and/or eruca concentrate or extract (on a solvent-free basis).

Suitable nutritional compositions comprising the above-mentioned plant/vegetable extracts or concentrates represent a further object of the invention. They are characterized in that they comprise (a) at least one plant/vegetable extract or concentrate selected from the group consisting of allium, petroselinum, brassica and eruca extracts and concentrates, (b) a calcium source, and (c) at least one energy source selected from the group consisting of carbohydrate, fat and nitrogen sources, and optionally (d) Vitamin D.

Regarding component (a), the definitions, preferences and amounts given before for the allium, petroselinum, brassica and eruca extracts and concentrates apply. It is also possible to have a mixture of two or more of said plant/vegetable extracts and concentrates as component (a). The nutritional compositions of the invention conveniently comprise (in % by weight) for example from approximately 0.1 to 40%, preferably from approximately 3 to 25% and most preferred from 5 to 15% of plant/vegetable extract or concentrate component (a).

The calcium source (b) may comprise any physiological acceptable inorganic or organic compound containing calcium. Examples are inorganic calcium salts, for example calcium chloride, calcium phosphate, calcium sulfate, calcium oxide, calcium hydroxide or calcium carbonate, or organic calcium components like whole or skim milk powder, calcium caseinate or calcium salts of organic acids such as calcium citrate, calcium maleate, or mixtures thereof. The use of organic calcium compounds, particularly skim milk powder, calcium caseinate or mixtures thereof, as calcium source (b) is preferred. The amount of calcium component to be supplied may vary within wide ranges. In general, the inventive compositions comprise in one unit dosage from about 100 mg to 1000 mg, preferably 200 mg to 700 mg and most preferred 300 to 600 mg of calcium (on an elemental basis).

The nutritional compositions of the invention conveniently comprise (in % by weight) for example from approximately 1 to 60%, preferably from approximately 5 to 50% and most preferred from 10 to 40% of calcium component (b).

Suitable carbohydrate sources include for example maltodextrins, starch, lactose, glucose, sucrose, fructose, xylit and/or sorbit. In these forms the carbohydrates are both energy suppliers and sweeteners. The inventive compositions may contain one or more different carbohydrate sources.

Suitable fat sources include omega-6 polyunsaturated fatty acid sources, omega-3 polyunsaturated fatty acid sources, mono-unsaturated fatty acid sources, medium chain fatty acid sources (i.e. $C_6$–$C_{12}$-fatty acids); or mixtures thereof. The above-mentioned fatty acids may be employed in each case in form of the free acid, in mono-, di- or particularly in triglyceride form, or in form of a pharmacological or nutritional acceptable natural source.

Suitable natural sources of omega-6 polyunsaturated fatty acids include vegetable oils such as safflower oil, sunflower oil, soya oil, cotton oil and corn oil. Suitable natural sources of omega-3 polyunsaturated fatty acids include linseed oil and fish oils such as menhaden oil, salmon oil, mackerel oil, tuna oil codliver oil and anchovy oil.

Suitable natural sources of mono-unsaturated fatty acid sources are particularly omega-9 mono-unsaturated fatty acids, for example olives, canola, safflower (hybrids) and sunflower (hybrids).

A preferred fat source comprises triglyceride oils supplying the desired amounts of omega-6 polyunsaturated fatty acids and omega-3 polyunsaturated fatty acids and which are rich in the medium chain fatty acid residues (i.e. residues of $C_6$–$C_{12}$ fatty acid) and/or mono-unsaturated fatty acid residues. The inventive compositions may contain one or more different fat sources.

Examples of suitable nitrogen sources of the inventive nutritional compositions include sources containing nutritionally acceptable proteins such as soy bean derived proteins; milk proteins such as whey proteins or caseinates; and/or protein hydrolysates; and/or essential amino acids mixtures in free amino acid form or salt form; and/or compounds associated with the synthesis of polyamines, such as arginine, arginine precursors, omithine and the like, in free amino acid form or salt form.

Preferred nitrogen sources of the nutritional compositions are
  (i) soy bean derived proteins, which may be employed in the form of soy beans or in the form of any suitable soja extract or concentrate, for example in form of soy flour, dried soy sprouts, soybean milk, or as dried aqueous extract from soybeans; or
  (ii) milk proteins, for example whey derived proteins or caseinates which may be employed for example in the form of whey powder, caseinate salts such as calcium caseinate and/or whole or preferably skim milk powder and/or
  (iii) a mixture of essential amino acids and/or
  (iv) arginine as nitrogen source.

Milk proteins such as whey powder, caseinates, particularly calcium caseinate, and/or skim milk powder are another particularly preferred nitrogen source of the claimed nutritional compositions. The inventive compositions may contain one or more different nitrogen sources.

The nutritional compositions comprise (in % by weight) for example, from approximately 0.1% to 98,9%, preferably from approximately 1 to approximately 95%, and most preferred from 10 to 90% of energy source component (c).

The contribution of the nitrogen source, carbohydrate source and fat source to the caloric of the inventive nutritional compositions may vary within wide ranges. For example, the carbohydrate source provides for 30 to 70% of the total energy supply, the nitrogen source for 5 to 45% and the fat source for 0.1 to 15% of the total energy supply of the composition. In preferred compositions of the invention the carbohydrate source provides for 40 to 60% of the total energy supply, the nitrogen for 20 to 35% and the fat source for 3 to 12% of the total energy supply of the composition.

A preferred energy source (c) of the inventive compositions comprises
  30 to 70% of the total energy supply of one or more carbohydrate sources selected from the group consisting of maltodextrins, starch, lactose, glucose, sucrose, fructose, xylit and sorbit;
  5 to 45% of the total energy supply of one or more nitrogen sources selected from the group consisting of soy bean derived proteins, milk proteins, a mixture of essential amino acids and arginine and
  0.1 to 15% of the total energy supply of one or more fat sources comprising omega-3- and omega-6- polyunsaturated fatty acids.

A particularly preferred energy source (c) of the inventive compositions comprises
  40 to 60% of the total energy supply of one or more carbohydrate sources selected from the group consisting of maltodextrins, starch, lactose, glucose, sucrose, fructose, xylit and sorbit;
  20 to 35% of the total energy supply of one or more nitrogen sources selected from the group consisting of soy bean derived proteins, skim milk powder and caseinates; and
  3 to 12% of the total energy supply of one or more fat sources comprising omega-3- and omega-6- polyunsaturated fatty acids.

The amount of Vitamin D (optional component (d)) to be supplied may vary within wide ranges. In general, the inventive compositions comprise in one unit dosage from about 400 IU to 1000 IU, preferably about 500 IU.

The nutritional formulations of the invention may comprise other nutritionally acceptable components such as vitamins, minerals, trace elements, fibers (preferably soluble fibers), flavors, preservatives, colorants, sweeteners, emulsifiers and the like.

Examples of vitamins suitable for the incorporation in the composition of the invention include Vitamin A, Vitamin D, Vitamin E, Vitamin K, Vitamin C, folic acid, thiamin, riboflavin, Vitamin $B_6$, Vitamin $B_{12}$, niacin, biotin and panthotenic acid in pharmaceutical or nutritionally acceptable form.

Examples of mineral elements and trace elements suitable for the incorporation in the composition of the invention include sodium, potassium, phosphorous, magnesium, copper, zinc, iron, selenium, chromium and molybdenum in pharmaceutical or nutritionally acceptable form.

The term soluble fiber as used herein refers to fibers which are able to substantially undergo fermentation in the colon to produce short chain fatty acids. Examples of suitable soluble fibers include agar-agar, alginates, carubin, carrageenan, gum arabic, guar gum, karaya gum, locust bean gum, pectin, tragacanth, or xanthan gum. They may be hydrolysed or not.

Suitable flavors include natural or artificial flavors, for example fruit flavors such as banana, orange, peach, pineapple or rasberry; vegetable flavors; or vanilla, cocoa, chocolate, coffee and the like.

Preferred ingredients of the inventive nutritious compositions in addition to components (a), (b), (c) and (d) comprise beta-carotene (Vitamin A), Vitamin E, Vitamin C, thiamin, Vitamin $B_1$, $B_6$ and/or $B_{12}$, potassium, magnesium, selenium, zinc, phosphorous and soluble fiber in pharmaceutical or nutritionally acceptable form.

The nutritional compositions may comprise (in % by weight) for example, from approximately 0.1% to 15%, preferably from approximately 0.2 to approximately 10%, and most preferred from 0.5 to 5% of these additional components other than components (a), (b), (c) and optionally (d).

The inventive nutritional formulations may be formulated and administered in any form suitable for enteral administration, for example oral administration or tube feeding, e.g. nasal administration. The formulations are conveniently administered in the form of an aqueous liquid. The formulations suitable for enteral application are accordingly preferably in aqueous form or in powder or granulate form, whereby the powder or granulate is conveniently added to water prior to use. For use as tube feeding, the amount of water to be added will i.a. depend on the patient's fluid requirements and condition.

The inventive nutritional compositions may be in form of a complete formula diet (in liquid or powder form), such that, when used as sole nutrition source essentially all daily caloric, nitrogen, fatty acids, vitamin, mineral and trace element requirements are met. In general, the daily amount to be supplied to adult persons will lie in the range of 750 to 3500 kcal/day, in particular of 1000 to 2000 kcal/day. However, the inventive nutritional compositions are preferably intended for use as a dietary supplement. The amount of energy supplied by a supplement should not be too excessive, in order not to unnecessarily suppress the patients appetite. The supplement conveniently comprises energy sources in an amount supplying from 50 to 1500 kcal/day, preferably 100 to 900 kcal/day and most preferred 150 to 700 kcal/day.

The nutritional compositions of the invention which are in liquid form, for example in drink form, or preferably in solid form, for example in granulate or powder form, may be obtained in a manner known per se, e.g. by admixing the ingredients and optionally adding water.

The invention further relates to pharmaceutical compositions in single dose unit form comprising (a) at least one plant/vegetable extract or concentrate selected from the group consisting of allium, petroselinum, brassica and eruca extracts and concentrates, and (b) a pharmaceutical acceptable carrier.

These pharmaceutical compositions are compositions for enteral administration, such as oral, nasal or rectal administration. Suitable pharmaceutical compositions may be in liquid form or preferably in solid form and comprise (in % by weight) for example, from approximately 0.001% to 100%, preferably from approximately 0.1 to approximately 50%, active ingredient (a).

The active ingredient (a) is a plant/vegetable extract or concentrate selected from the group consisting of allium, petroselinum, brassica and eruca extracts and concentrates where the above-given definitions and preferences apply. It is also possible to have a mixture of two or more of said plant/vegetable extracts and concentrates a).

Pharmaceutical compositions for enteral administration are, for example, those in single dose unit forms, such as dragees, tablets, capsules or sachets. They are prepared in a manner known per se, for example by means of conventional mixing, granulating, confectioning, dissolving or lyophilising processes.

For example, pharmaceutical compositions for oral administration can be obtained by combining the active ingredient with solid carriers, optionally granulating a resulting mixture and processing the mixture or granules, if desired or necessary after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, com, wheat, rice or potato starch, gelatin, tragacanth, methylcellulose and/or polyvinylpyrrolidone, and, if desired, disintegrators, such as the above-mentioned starches, and also carboxymethyl starch, cross-linked polyvinylpyrrolidone, agar, or alginic acid or a salt thereof, such as sodium alginate. Excipients are especially flow-conditioners and lubricants, for example silicic acid, talc, stearic acid or salts thereof, such as magnesium or calcium stearate, and/or polyethylene glycol. Dragee cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Dyes or pigments may be added to the tablets or dragee coatings, for example for identification purposes or to indicate different doses of active ingredient.

Other orally administrable pharmaceutical compositions are hard gelatin capsules and also soft, sealed capsules consisting of gelatin and a plasticiser, such as glycerol or sorbitol. The hard gelatin capsules may comprise the active ingredient in the form of granules, for example in admixture with fillers, such as lactose, binders, such as starches, and/or glidants, such as talc or magnesium stearate, and, if desired, stabilisers. In soft capsules the active ingredient is preferably dissolved or suspended in suitable liquids, such as fatty oils, paraffin oil or liquid polyethylene glycols, it is likewise being possible to add stabilisers.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylen glycols or higher alkanols. It is also possible to use gelatin rectal capsules which comprise a combination of the active ingredient with a base material. Suitable base materials are, for example, liquid triglycerides, polyethylenglycols or paraffin hydrocarbons.

The inhibitory effect on bone resorption of the inventive plant or vegetable extracts and concentrates may be assessed by measuring the urinary excretion of [$^3$H]-tetracycline from chronically prelabled rats as described in R. C. Mühlbauer and H. Fleisch, Am J Physiol 258, R679–R689 (1990). The method is based on the characteristics (i) that $^3$H-labeled tetracycline is deposited in hard tissues during their formation; and (ii) when bone is resorbed, [$^3$H]-tetracycline is released, circulates in blood, and is excreted into the urine where it can be assessed by counting $^3$H. This is probably due to the fact that [$^3$H]-tetracycline from bone circulates in a form that binds poorly to hydroxyapatite and, therefore, [³H]-tetracycline once liberated from bone, is only poorly reutilized during bone turnover, and because of an efficient renal excretion. The method may be performed as follows: rats are injected subcutaneously twice a week with increasing volumes of a solution containing [³H]-tetracycline starting shortly after birth until the age of about six weeks. At the age of about 50 days, the animals are transferred to individual metabolic cages and every rat is fed with the same amount of a standardized diet for about the three weeks. After that, one group of rats is fed with a purified diet, and another group is fed with the purified diet containing in addition a certain amount of an inventive plant or vegetable concentrate or extract. During the experiments, the animals have free access to demineralized water.

When the rats are about 60 days old, daily 24-hour urine collections are started, and the ³H contents in urine are determined by liquid scintillation counting. A diagram is then prepared wherein the [³H]-tetracycline contents in urine of the two groups of rats are plotted as a function of time (days).

Suitable experiments show that the plant or vegetable extracts and concentrates of the invention are capable of considerably decreasing the cumulative [³H]-tetracycline excretion in urine of intact males and castrated female rats which indicates a high inhibitory effect on bone resorption. Accordingly, the claimed nutritional and pharmaceutical compositions are useful for the treatment and prophylaxis of all kinds of diseases or conditions which are characterized by increased bone resorption, such as Paget's disease, tumor-induced bone disease or particularly osteoporosis.

The inhibitory effect of the plant or vegetable extracts or concentrates on bone resorption may also be assessed by an in vitro assay (described in Example 3) in which ivory slices, onto which freshly isolated osteoclasts have been settled, are incubated with a medium containing the extract or concentrate to be tested. The inhibitory effect on osteoclasts is assessed by counting the osteoclast resorption pits on the ivory slice.

In the following Examples, which illustrate the invention, % are parts by weight unless stated otherwise, and temperatures are given in ° C.

EXAMPLE 1

The following is an example of a suitable composition of an inventive Supplement in powder form.

| Supplement in Powder Form (1 portion) | |
|---|---|
| Content | 65.0 g |
| Inventive Extract/Concentrate[1]) including carbohydrates, protein and fiber | 14.5 g |
| Protein including | 20.0 g |
| Ca-caseinate protein | 8.7 g |
| skim milk powder | 11.0 g |
| Fat including | 2.8 g |
| omega-6 polyunsaturated acids | 1.3 g |
| omega-3 polyunsaturated acids | 0.03 g |
| Carbohydrates (including inventive extract) including | 31.0 g |
| lactose | 16.5 g |
| maltodextrin | 3.5 g |
| Fiber (soluble) | 5.0 g |
| Further ingredients including | 3.0 g |
| Na | 230 mg |
| K | 500 mg |
| Ca | 600 mg |
| Mg | 90 mg |

-continued

| Supplement in Powder Form (1 portion) | |
|---|---|
| P | 430 mg |
| Cl | 350 mg |
| Zn | 150 mg |
| Retinol (vitamin A) | 0.3 mg |
| Calciferol (vitamin D) | 5.0 mcg |
| Tocopherol (vitamin E) | 3.0 mg |
| Phylloquinone (vitamin K1) | 30.0 mcg |
| Thiamin (vitamin B1) | 0.4 mg |
| Riboflavin (vitamin B1) | 0.5 mg |
| Pyridoxine (vitamin B6) | 0.8 mg |
| Cyanocobalamin (vitamin B12) | 0.8 mcg |
| Ascorbic acid (vitamin C) | 20.0 mg |
| Biotin | 50.0 mcg |
| Folic acid | 120.0 mcg |
| Niacinamide | 5.0 mg |
| Panthothenic acid | 2.0 mg |
| Energy value | 229 kcal |

[1]a) Extract 1 obtained by extracting 48.3 g dry broccoli for 10 minutes at 89 ± 3° C. with 483 ml distilled water and then evaporating the extract to dryness.
b) Extract 2 obtained by extracting 48.3 g dry Italian Parsley for 10 minutes at 89 ± 3° C. with 483 ml distilled water and then evaporating the extract to dryness.
c) Extract 3 obtained by extracting 26.4 g dry onions for 10 minutes at 89 ± 3° C. with 264 ml distilled water and then evaporating the extract to dryness.
d) Extract 4 obtained by extracting 58.9 g dry onions for 10 minutes at 89 ± 3° C. with 589 ml distilled water and then evaporating the extract to dryness, followed by a second extraction of the dried water extract with 324 ml of 85% ethanol/15% water for one hour at 60° C., cooling to room temperature and keeping over night at −20° C., decanting the supernatant, evaporating the alcohol and freeze-drying the extract.
e) Extract 5 obtained by extracting 45.3 g dry onions for one hour at 60° C. with 453 ml of 85% ethanol/15% water, filtrating, evaporating the alcohol and freeze-drying the extract.
f) Concentrate 6 obtained by drying fresh bear's garlic and grinding it to a fine powder.

The above supplement may be mixed with water and taken in appropriate concentration between meals.

EXAMPLE 2

Effect of $H_2O$ Extracts of Broccoli, Dog-parsley and Onion on Bone Resorption The effect of the inventive plant or vegetable extracts and concentrates on bone resorption is based on a method as described in R. C. Mühlbauer and H. Fleisch, Am J Physiol 259, R679–R689 (1990). Bone resorption is monitored by the urinary excretion of ³H in Wistar rats prelabled from birth for 6 weeks with [³H]-tetracycline as described in the above-mentioned reference. The rats are then housed in individual metabolic cages and are fed for 10 days with a standard laboratory chow (Kliba 331, Klingentalmühle, Kaiseraugst, Switzerland) containing 1.0 g Ca, 0.7 g P, and 80 IU of vitamin $D_3$/100 g of food. After this adaptation period, all rats received a diet containing 1.0 g Ca, 1.2 g P, and 80 IU of vitamin $D_3$/100 g dry weight. This was achieved by adding appropriate amounts of Ca-gluconate and neutral phosphate salts to a basic low calcium, low phosphate diet (Sodi 2134, Klingenthalmühle, Kaiseraugst, Switzerland) in powder form for another 10 days during which urine is collected. Then rats were "pair-fed" receiving 28 g of wet food per day. One group (n=6) is switched to a purified diet ("Diet P", Sodi 2160, Klingenthalmühle, Kaiseraugst, Switzerland given as wet food with a water content of 45±2% containing 1.0 g Ca, 1.2 g P, and 80 IU of vitamin $D_3$/100 g dry weight), a second group (n=5) is fed with the purified diet containing in addition 300 mg extract from broccoli per day (corresponding to 1.0 gram of dry broccoli extracted for 10 minutes at 89±3° C. with 10 ml distilled water), a third group (n=5) is fed with the purified diet containing in addition 300 mg extract from Italian Parsley per day (corresponding to 1.0 gram of dry Italian Parsley extracted for 10 minutes at 89±3° C. with 10 ml distilled water), and a fourth group (n=5) is fed with the purified diet containing in addition 550 mg extract from onion per day (corresponding to 1.0 gram of dry onion extracted for 10 minutes at 89±3° C. with 10 ml distilled water).

After 10 days adaptation without urine collection and a further 10 days with urine collection, the rats are allocated to the different treatment groups. Using the baseline 24 hour [$^3$H]-tetracycline excretion as selection criterion, special care is taken to obtain similar mean initial values for each group. Thereafter, the rats are switched to the purified diet with or without inventive extract and daily 24-hour urine collections are performed over a period of 14 days, and the cumulative [$^3$H]-tetracycline excretion in urine is determined by liquid scintillation counting.

After 14 days of treatment the cumulative bone resorption was 9.2%, 9.5% and 17.5% ($p<0.05$) lower as compared to the control group, in rats daily fed the extracts of broccoli, Italian Parsley and onion respectively.

EXAMPLE 3

Effect of a Bear's Garlic Concentrate on Bone Resorption

The same method as described in Example 2 is used except that treatment lasts only six days and the test group (n=5) is fed with the purified diet containing in addition 1 g of a concentrate from bear's garlic (obtained by drying and grinding fresh bear's garlic). It was found that bear's garlic inhibits bone resorption in male rats by 13.5% ($p<0.05$).

EXAMPLE 4

Effect of Onion Extract on in Vitro Resorption

The effect of an onion extract on in vitro resorption is investigated on osteoclast-mediated resorption (as described in Arnett TR, Spowage M, 1996, Modulation of the resorptive activity of rat osteclasts by small changes in extracellular pH near the physiological range. Bone 18:277–279) with the following modifications: instead of using bone wafers, ivory slices are used as mineral substrate to assess osteoclast resorption pits which are counted under tangential illumination after gold spottering (Vitté C, Fleisch H, Guenther H L, 1996, Bisphosphonates induce osteoblasts to secrete an inhibitor of osteoclast-mediated resorption, Endocrinology 137:2324–2333). In this assay one 4×4 millimeter ivory slice, onto which freshly isolated osteoclasts have been settled is incubated per well of a 48-well plate in 250 µl of a medium containing the extract to be tested during 24 hours at 37° C. in a 5% $CO_2$/air atmosphere. For each dose 8 slices are used. Osteoclasts are harvested from femurs of newborn rats which are, after removing the cartilagenous ends, split in half and chopped transversally. This procedure leads to a cell suspension rich in other cells such as osteoblasts. This permits to test effects in broad conditions, that is, as to both, direct effect on osteoclast and indirect effect on the osteoclast mediated by other cells such as osteoblasts.

The onion extract is obtained by extracting a fine powder of onion for 10 minutes in distilled water (100 g/l) at 90° C., filtrating and freeze-drying the filtrate, followed by a second extraction of the dry water extract for one hour at 60° C. in 85% ethanol/15% water, cooling to room temperature, keeping over night at −20° C. to allow precipitation of unwanted material, decanting the supernatant, evaporating the alcohol and freeze-drying the thus obtained residue, whereby 250 mg freeze-dried onion extract are obtained for each g of dry whole onion.

The onion extract (0.017, 0.17, 1.7 mg onion extract/ml medium) inhibited osteoclast-mediated resorption of dentine in a dose-dependent manner, while the number of tartrate-resistant alcaline phosphatase positive (TRAP$^+$) multinucleated cells (MNC) did not decrease significantly. Thus, the ratio pits/TRAP$^+$ MNC decreased significantly ($p<0.001$). From this it is concluded that the presence of large numbers of TRAP$^+$ MNC in these cultures despite the additions of onion extract indicate that onion extract is not toxic to these cells but rather inhibits the activity of osteoclasts.

What is claimed is:

1. A method for the treatment or prophylaxis of a disease or condition in a patient having the disease or condition which is characterized by increased bone resorption comprising administering to the patient an amount of a plant extract or concentrate selected from the group consisting of *Allium cepa, Allium ursinum, Petroselinum crispum crispum, Petroselinum crispum* var. neapolitanum, and *Brassica oleracea* var. italica, *Eruca sativa* and concentrates and mixtures thereof, effective to inhibit or reduce bone resorption, in a medicament or nutritional formulation, wherein said plant extract and concentrate are produced by extracting with an aqueous solvent.

2. The method of claim 1, wherein the medicament or nutritional formulation further comprises a calcium source and an energy source.

3. The method of claim 2, wherein the energy source is selected from the group consisting of a fat source, carbohydrate source and a nitrogen source.

4. The method of claim 3, wherein the medicament or nutritional formulation further comprises a Vitamin D source.

5. The method of claim 3, wherein the carbohydrate source is selected from the group consisting of maltodextrin, starch, lactose, glucose, sucrose, fructose, xylitol, sorbitol, and mixtures thereof.

6. The method of claim 2, wherein the calcium source is an organic calcium salt.

7. The method of claim 1, wherein the disease or condition which is characterized by increased bone resorption is selected from the group consisting of Paget's disease, tumor-induced bone disease and osteoporosis.

8. The method of claim 1, wherein the amount of a plant extract or concentrate is in solid form.

9. A method for the treatment or prophylaxis of a disease or condition in a patient having the disease or condition which is characterized by increased bone resorption comprising administering to the patient an amount of a plant extract or concentrate selected from the group consisting of Petroselinum and Eruca and concentrates and mixtures thereof, effective to inhibit or reduce bone resorption, in a medicament or nutritional formulation, wherein said plant extract and concentrate are produced by extracting with an aqueous solvent.

10. The method of claim 9, wherein the medicament or nutritional formulation further comprises a calcium source and an energy source.

11. The method of claim 10, wherein the energy source is selected from the group consisting of a fat source, carbohydrate source and a nitrogen source.

12. The method of claim 11, wherein the medicament or nutritional formulation further comprises a Vitamin D source.

13. The method of claim 11, wherein the carbohydrate source is selected from the group consisting of maltodextrin, starch, lactose, glucose, sucrose, fructose, xylitol, sorbitol, and mixtures thereof.

14. The method of claim 10, wherein the calcium source is an organic calcium salt.

15. The method of claim 9, the disease or condition which is characterized by increased bone resorption is selected from the group consisting of Paget's disease, tumor-induced bone disease and osteoporosis.

16. The method of claim 9, wherein the plant extract or concentrate is in solid form.

17. A method for the treatment of prophylaxis of a disease or condition in a patient having the disease or condition which is characterized by increased bone resorption comprising administering to the patient an amount of a plant extract or concentrate of *Allium cepa*, effective to inhibit or reduce bone resorption, in a medicament or nutritional formulation, wherein said plant extract and concentrate are produced by extracting with a solvent comprising water and alcohol.

18. The method of claim 17, wherein the medicament or nutritional formulation further comprises a calcium source and an energy source.

19. The method of claim 18, wherein the energy source is selected from the group consisting of a fat source, carbohydrate source and a nitrogen source.

20. The method of claim 19, wherein the medicament or nutritional formulation further comprises a Vitamin D source.

21. The method of claim 19, wherein the carbohydrate source is selected from the group consisting of maltodextrin, starch, lactose, glucose, sucrose, fructose, xylitol, sorbitol, and mixtures thereof.

22. The method of claim 18, wherein the calcium source is an organic calcium salt.

23. The method of claim 17, wherein the disease or condition which is characterized by increased bone resorption is selected from the group consisting of Paget's disease, tumor-induced bone disease and osteoporosis.

24. The method of claim 17, wherein the plant extract or concentrate is in solid form.

* * * * *

UNITED STATES PATENT AND TRADEMARK OFFICE
CERTIFICATE OF CORRECTION

PATENT NO.   : 6,638,540 B2
DATED         : October 28, 2003
INVENTOR(S)  : Roman Conrad Muhlbauer It is certified that error appears in the above-identified patent and that said Letters Patent is hereby corrected as shown below:

<u>Title page,</u>
Item [75], Inventor, the inventor country code "(SE)" should be -- (CH) --.
OTHER PUBLICATIONS, "Y.P. Chen," reference, the word "Iraumatology" should be -- Traumatology --.

<u>Column 13,</u>
Line 7, after the number "9," insert -- wherein --.

Signed and Sealed this

Fourth Day of May, 2004

JON W. DUDAS
*Acting Director of the United States Patent and Trademark Office*